United States Patent [19]

Wohlleben et al.

[11] Patent Number: 4,918,015
[45] Date of Patent: Apr. 17, 1990

[54] GENTAMICIN-RESISTANCE GENES AND THEIR USE AS MARKERS

[75] Inventors: Wolfgang Wohlleben; Günter Muth; Alfred Pühler, all of Bielefeld, Fed. Rep. of Germany

[73] Assignee: Hoechst Aktiengesellschaft, Frankfurt am Main, Fed. Rep. of Germany

[21] Appl. No.: 44,325

[22] Filed: Apr. 30, 1987

[30] Foreign Application Priority Data

May 2, 1986 [DE] Fed. Rep. of Germany ....... 3614903

[51] Int. Cl.⁴ .................. C12N 1/20; C12N 7/00; C12P 21/00; C12R 1/465
[52] U.S. Cl. .................. 435/172.3; 536/27; 435/320; 435/252.3; 435/252.35; 435/886; 935/29; 935/56
[58] Field of Search ............. 935/29, 56; 435/68, 435/91, 320, 886, 172.3; 536/252.3, 252.35, 13.6, 27

[56] References Cited

U.S. PATENT DOCUMENTS 4,332,900 6/1982 Manis et al. .................. 435/172

OTHER PUBLICATIONS

Hirsch & Beringer, A Physical Map of pPH1JI and pJB4JI, Plasmid 12, 139-141 (1984).
Vieira & Messing, the pUC Plasmids an M13mp 7-Derived System for Insertion Mutagenesis and Sequencing with Synthetic Universal Primers, Gene, 19 pp. 259-268 (1982).
Yangsch-Perron et al., Improved M13 phage Cloning Vectors and Host Strains: Nucleotide Sequences of the M13mp18 and pUC19 Vectors, Gene, 33 (1985), 103-119.

*Primary Examiner*—Thomas G. Wiseman
*Assistant Examiner*—S. L. Nolan
*Attorney, Agent, or Firm*—Finnegan, Henderson, Farabow, Garrett and Dunner

[57] ABSTRACT

*S. ghanaensis* DSM 2932 is resistant to gentamicin at up to 20 μg/ml. Total digestion of the genomic DNA with BglII, incorporation of the restriction fragments into a suitable plasmid, and selection using gentamicin results in gentamicin-resistant clones which contain a 7 kb fragment with the gentamicin-resistance gene. The plasmid pPH1JI likewise contains a gentamicin-resistance gene located on a 2.3 kb HindIII-BamHI fragment. These genes are suitable as markers, in particular for Streptomycetes vectors.

31 Claims, 2 Drawing Sheets

GENTAMICIN-RESISTANCE GENES AND THEIR USE AS MARKERS

BACKGROUND OF THE INVENTION

The number of resistance genes available to date for cloning in Streptomycetes is relatively small, and some of them are additionally subject to special restrictions. Thus, for example, hygromycin is highly toxic, viomycin is no longer commercially available, and chloramphenicol is suitable only in special cases because of the known instability of the resistance gene in Streptomycetes. Thus there is a need for further resistance markers.

Many Streptomycetes are extremely sensitive to the antibiotic gentamicin. Thus, as a rule, growth on the plate is inhibited at a gentamicin concentration of only 0.5 μg/ml.

SUMMARY OF THE INVENTION

The present invention relates to two gentamicin-resistance genes which are active and stable in Streptomycetes and have a number of cleavage sites suitable for insertion inactivation.

DETAILED DESCRIPTION OF THE PREFERRED EMBODIMENTS

It has been found that the Streptomycetes strain *S. ghanaensis* DSM 2932 tolerates the unusually high dose of 20 μg/ml gentamicin. This strain is mentioned in the European patent applications with the publication Nos. 0,158,201 and 0,158,872. This strain contains the plasmid pSG5. It has also been found that the gentamicin resistance is located on an approximately 7 kb BglII fragment. Total digestion of the DNA from the strain DSM 2932, ligation of the fragments into a suitable vector and selection for gentamicin resistance result in isolation of the hybrid vector which contains the 7 kb fragment incorporated.

It has also been found that the plasmid pGM2 (European Patent Application 0,158,872, FIG. 3) is particularly well suited as a vector for isolating the 7 kb fragment from the genome of *S. ghanaensis* DSM 2932. For this purpose, the vector pGM2 is linearized with the restriction enzyme BglII and treated with the enzyme alkaline phosphatase. The total DNA from the strain DSM 2932 is likewise completely digested with BglII and, without fractionation by size, ligated with the linearized plasmid pGM2. The ligation mixture is transformed into a suitable strain of Streptomycetes sensitive to gentamicin. After incubation for a sufficient time, the regeneration plates are covered with soft agar containing thiostreptone. After further incubation, replica plating on gentamicin-containing agar is carried out. This results in isolation of clones which contain both thiostreptone resistance from the plasmid pGM2 and gentamicin resistance from the genome of DSM 2932. Plasmid isolation and retransformation of the plasmid DNA into a gentamicin-sensitive strain produces only thiostreptone- and gentamicin-resistant colonies. Restriction analysis demonstrates that the 7 kb fragment of FIG. 1 is present.

Suitable gentamicin-sensitive strains are *S. ghanaensis* strains such as ATCC 14672 (U.S. Pat. Nos. 3,674,866 and 4,621,061) as well as other Streptomycetes species such as *S. coelicolor, S. lividans, S. prasinus, S. venezuelae* and *S. geysirensis*.

Figure 1:
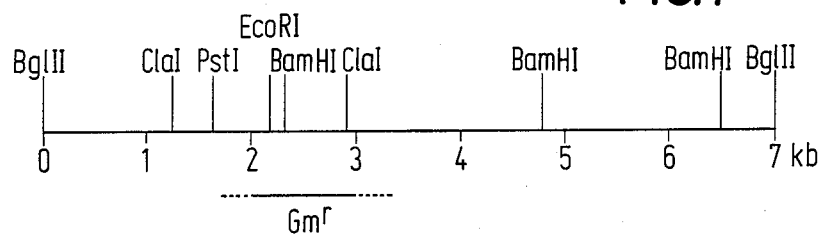
FIG. 1 shows the restriction map of an approximately 7 kb BglII fragment obtained from *S. ghanaensis*, strain DSM 2932.
Figure 2:
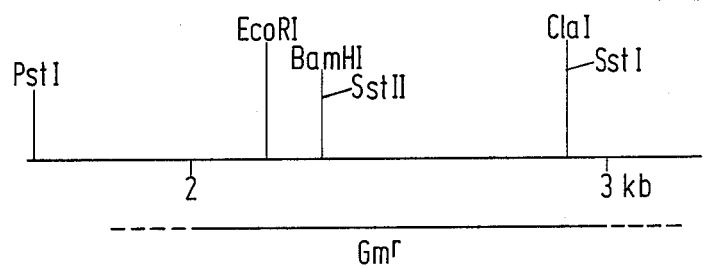
FIG. 2 is a detail of FIG. 1 and particularizes the coding region.

A number of cleavage sites are indicated on the restriction map shown in FIG. 1, including unique cleavage sites for PstI and EcoRI. More specifically, FIG. 1 shows a sequence of restriction sites for the 7 kb BglII fragment comprising, between two BglII ends, a sequence ClaI-PstI-EcoRI-BamHI-ClaI-BamHI-BamHI. FIG. 1 further shows that the DNA sequence that is capable of conferring a gentamicin-resistance ("Gmr") activity upon a host comprises, at least, the sequence of restriction sites EcoRI-BamHI-ClaI. This allows further localization of the gentamicin-resistance gene. BamHI, EcoRI, ClaI, SstI and SstII are suitable for insertion inactivation (FIG. 2).

Not only is this new marker gene distinguished by its large number of cleavage sites which can be used but, since it is a gene intrinsic to Streptomycetes, it may be expected that the vectors provided with it will be particularly stable.

Figure 3:
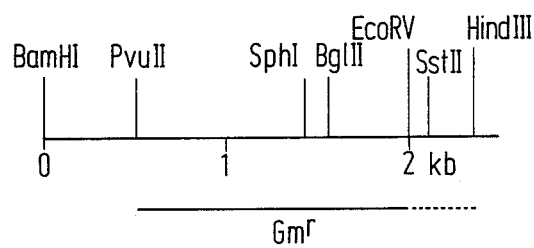
FIG. 3 show the linearized plasmid pGM2.

It has also been found, surprisingly, that the *E. coli* plasmid pPH1JI (P. R. Hirsch and J. E. Beringer, Plasmid 12 (1984) 139–141) also contains a gentamicin-resistance gene which is active and stable in Streptomycetes. Digestion with the enzymes HindIII and BamHI results in a 2.3 kb fragment on which the resistance gene is located (FIG. 3).

The promoter belonging to the resistance gene is located on this 2.3 kb fragment and is recognized not only by the RNA polymerase of Gram-negative bacteria but, unexpectedly, also by the RNA polymerase of Streptomycetes. Hence this gene is suitable for the construction of shuttle vectors which replicate both in Gram-negative bacteria and in Streptomycetes.

The cleavage sites for SphI and BglII are available for cloning with insertion inactivation.

The gentamicin-resistance gene from the plasmid pPH1JI is also expressed in Corynebacteria. Thus the statement "active in Streptomycetes" should by no means be interpreted in the sense that this activity is confined to Streptomycetes.

Since the natural Streptomycetes plasmids hitherto known contain no resistance markers suitable for applications in gene manipulation, the invention provides further possibilities for genetic engineering with Streptomycetes vectors.

EXAMPLE 1

The plasmid pGM2 (European Patent Application 0,158,872, page 3, paragraph 3, and FIG. 3) is linearized with BglII and reacted with the enzyme alkaline phosphatase (from calf intestines).

The total DNA from *S. ghanaensis* DSM 2932 is completely digested with BglII and combined with the pGM2 digestion mixture, and T4 DNA ligase is added thereto.

The ligation mixture is transformed into *S. lividans* TK 23 (obtainable from the John Innes Foundation, Norwich, Britain) (K. F. Chater, D. A. Hopwood, T. Kieser and C. J. Thompson: Gene Cloning in Streptomyces, Current Topics in Microbiol. and Immunol. 96, 69–95 (1982)). After 18 hours, the regeneration plates are covered with thiostreptone-containing soft agar. After one week, replica plating on agar containing 5 μg/ml gentamicin is carried out. This results in isolation of a clone resistant to both thiostreptone and gentamicin.

Figure 4:
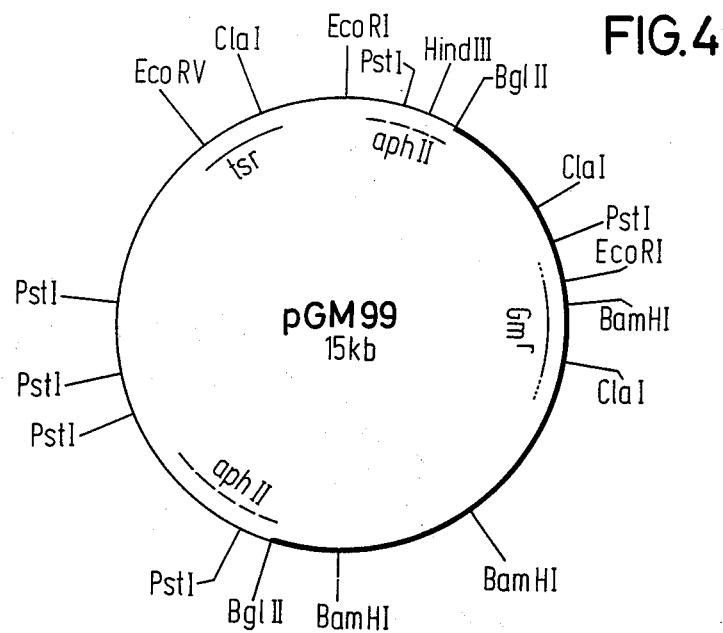
FIG. 4 shows the linearized plasmid pGM99.

Plasmid isolation and retransformation of the plasmid DNA into S. lividans TK 23 results in only thiostreptone- and gentamicin-resistant colonies (193 of 193 transferred colonies). Restriction analysis shows insertion of the 7 kb fragment as depicted in FIG. 1. FIG. 4 shows the isolated plasmid pGM99, which is a molecule about 15 kilobases in size and which confers resistance to thiostreptone and gentamicin.

EXAMPLE 2

Figure 5:
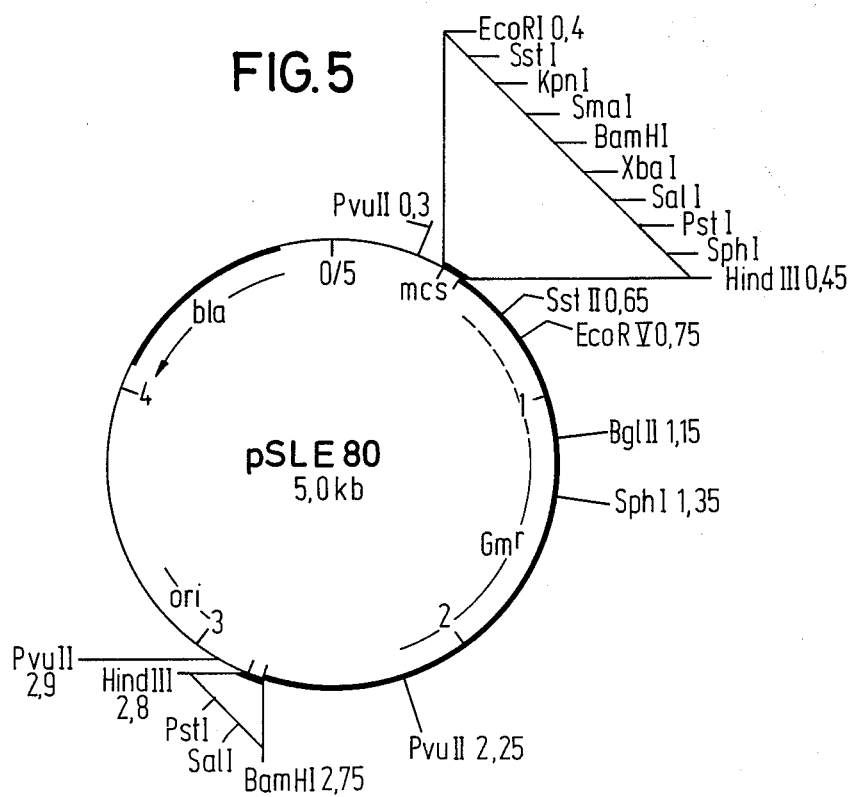
FIG. 5 shows the restriction map of plasmid pSLE80.

Total digestion of pPH1JI (Hirsch et al., loc. cit.) with BamHI results in the 3.6 kb fragment with the gentamicin-resistance gene. This fragment is ligated into pUC8 which has been opened with BamHI, resulting in the plasmid R189-2. Cutting of this plasmid with HindIII results in a 2.4 kb fragment. This fragment is ligated into pUC19 which has been opened with HindIII, resulting in the plasmid pSLE80 (FIG. 5). This plasmid is deposited (in E. coli JM 83) at the Deutsche Sammlung für Mikroorganismen (German Collection of Microorganisms) under the number DSM 3710.

The gentamicin-resistance gene can be reisolated and cloned by cutting with suitable enzymes.

We claim:

1. A substantially pure DNA fragment comprising a nucleotide sequence that comprises a sequence of restriction sites wherein said sequence includes EcoRI-BamHI-ClaI, said DNA fragment is capable of conferring a gentamicin-resistance activity to a host and said host is gentamicin-sensitive.

2. A DNA fragment as claimed in claim 1, wherein said nucleotide sequence further comprises restriction sites for SstII and SstI.

3. A DNA fragment as claimed in claim 1, wherein said host is a strain of Streptomycetes.

4. A DNA fragment as claimed in claim 3, wherein said strain of Streptomycetes is selected from the group consisting of S. ghanaensis, S. coelicolor, S. lividans, S. prasinus, S. venezuelae and S. geysirensis.

5. A DNA fragment as claimed in claim 1, wherein said gentamicin-resistance activity comprises the ability to tolerate a dose of at least 5 microgram/ml of gentamicin.

6. A vector comprising a DNA fragment as claimed in claim 1, wherein said vector is capable of being transferred to a host, replicating in the host and conferring a gentamicin-resistance activity upon the host and said host is gentamicin-sensitive.

7. A vector as claimed in claim 6, wherein said host is a strain of Streptomycetes.

8. A vector as claimed in claim 7, wherein said strain of Streptomycetes is selected from the group consisting of S. ghanaensis, S. coelicolor, S. lividans, S. prasinus, S. venezuelae and S. geysirensis.

9. A transformed host comprising a vector as claimed in claim 6, wherein said transformed host is capable of exhibiting a gentamicin-resistance activity.

10. A transformed host as claimed in claim 9, wherein said gentamicin-resistance activity comprises the ability to tolerate a dose of at least 5 microgram/ml of gentamicin.

11. A transformed host as claimed in claim 9, wherein said host is a strain of Streptomycetes.

12. A transformed host as claimed in claim 11, wherein said strain of Streptomycetes is selected from the group consisting of S. ghanaensis, S. coelicolor, S. lividans, S. prasinus, S. venezuelae and S. geysirensis.

13. A process for conferring a gentamicin-resistance activity upon a host comprising the steps of
  (a) inserting a DNA fragment as defined in claim 1 into a plasmid to form a hybrid plasmid, wherein said hybrid plasmid is capable of being transferred to a host, of replicating in the host and of conferring upon the host a gentamicin-resistance activity and
  (b) transforming the host with the hybrid plasmid.

14. A process as claimed in claim 13, wherein said host is a strain of Streptomycetes.

15. A substantially pure DNA fragment comprising a nucleotide sequence that is capable of conferring a gentamicin-resistance activity upon a host, wherein said DNA fragment is produced by the process comprising the steps of
  (a) substantially digesting DNA from S. ghanaensis, strain DSM 2932, with BglII to produce fragments of S. ghanaensis DNA,
  (b) incorporating a fragment of the BblII-digested S. ghanaensis DNA into a plasmid to produce a hybrid plasmid that is capable of being transferred to a host, of replicating in the host and of conferring gentamicin-resistance activity upon the host,
  (c) selecting the hybrid plasmid that is capable of conferring the gentamicin-resistance activity upon the host and
  (d) isolating the DNA fragment from the hybrid plasmid,
wherein said host is gentamicin-sensitive.

16. A DNA fragment as claimed in claim 15, wherein step (c) comprises the steps of
  (1) transferring the hybrid plasmid from step (b) to the host to produce a transformed host, and
  (2) selecting the transformed host that is capable of exhibiting the gentamicin-resistance activity.

17. A DNA fragment as claimed in claim 15, wherein said host is a strain of Streptomycetes.

18. A DNA fragment as claimed in claim 17, wherein said strain of Streptomycetes is selected from the group consisting of S. ghanaensis, S. coelicolor, S. lividans, S. prasinus, S. venezuelae and S. geysirensis.

19. A DNA fragment as claimed in claim 15, wherein said gentamicin-resistance activity comprises the ability to tolerate a dose of at least 5 microgram/ml of gentamicin.

20. A vector comprising a DNA fragment as claimed in claim 15, wherein said vector is capable of being transferred to a host, replicating in the host and conferring gentamicin-resistance activity upon the host, and said host is gentamicin-sensitive.

21. A vector as claimed in claim 20, wherein said host is a strain of Streptomycetes.

22. A vector as claimed in claim 21, wherein said strain of Streptomycetes is selected from the group consisting of S. ghanaensis, S. coelicolor, S. lividans, S. prasinus, S. venezuelae and S. geysirensis.

23. A transformed host comprising a vector as claimed in claim 20, wherein said transformed host is capable of exhibiting a gentamicin-resistance activity.

24. A transformed host as claimed in claim 23, wherein said gentamicin-resistance activity comprises the ability to tolerate a dose of at least 5 microgram/ml of gentamicin.

25. A transformed host as claimed in claim 23, wherein said host is a strain of Streptomycetes.

26. A transformed host as claimed in claim 25, wherein said strain of Streptomycetes is selected from the group consisting of *S. ghanaensis, S. coelicolor, S. lividans, S. prasinus, S. venezuelae* and *S. geysirensis.*

27. A process for conferring a gentamicin-resistance activity upon a host comprising the steps of
   (a) inserting a DNA fragment as defined in claim 15 into a plasmid to form a hybrid plasmid, wherein said hybrid plasmid is capable of being transferred to a host, of replicating in the host and of conferring upon the host a gentamicin-resistance activity and
   (b) transforming the host with the hybrid plasmid.

28. A process as claimed in claim 27, wherein said host is a strain of Streptomycetes.

29. A substantially pure DNA fragment comprising a nucleotide sequence that is capable of conferring a gentamicin-resistance activity upon a host and has a restriction map as shown in FIGS. 1 and 2.

30. A substantially pure DNA fragment comprising a DNA sequence that encodes a protein that is capable of effecting resistance towards gentamicin, wherein said sequence comprises a restriction map as shown in FIGS. 1 and 2.

31. A substantially pure DNA fragment comprising a nucleotide sequence coding for a protein that is capable of conferring a gentamicin-resistance activity upon a host, wherein said DNA fragment is produced by the process comprising the steps of
   (a) substantially digesting DNA from *S. ghanaensis*, strain DSM 2932, with BglII to produce fragments of *S. ghanaensis* DNA,
   (b) incorporating said fragments of *S. ghanaensis* DNA into a population of plasmids to produce a population of hybrid plasmids, wherein said hybrid plasmids are capable of being transferred to a host, of replicating in the host and of encoding a protein that is capable of effecting resistance to gentamicin in the host,
   (c) selecting a hybrid plasmid from among the population of hybrid plasmids and
   (d) isolating the DNA fragment from the hybrid plasmid selected, wherein said host is gentamicin sensitive.

* * * * *